US012649012B2

(12) United States Patent
Long

(10) Patent No.: US 12,649,012 B2
(45) Date of Patent: *Jun. 9, 2026

(54) ESSENTIAL OIL ATOMIZATION AND PUMPING APPARATUS

(71) Applicant: Jiwu Long, Shaoyang (CN)

(72) Inventor: Jiwu Long, Shaoyang (CN)

( * ) Notice: Subject to any disclaimer, the term of this patent is extended or adjusted under 35 U.S.C. 154(b) by 209 days.

This patent is subject to a terminal disclaimer.

(21) Appl. No.: 18/641,062

(22) Filed: Apr. 19, 2024

(65) Prior Publication Data

US 2025/0256002 A1 Aug. 14, 2025

(30) Foreign Application Priority Data

Feb. 11, 2024 (CN) .......................... 202420291089.0

(51) Int. Cl.
*A61L 9/03* (2006.01)
(52) U.S. Cl.
CPC ......... *A61L 9/037* (2013.01); *A61L 2209/133* (2013.01); *A61L 2209/134* (2013.01)
(58) Field of Classification Search
CPC ... A61L 9/02; A61L 9/03; A61L 9/037; A61L 2209/133; A61L 2209/134; A45D 2024/002; A45D 24/22; A45D 24/28
See application file for complete search history.

(56) References Cited

U.S. PATENT DOCUMENTS

| | | | | |
|---|---|---|---|---|
| 2018/0117203 A1* | 5/2018 | Gruenbacher | ...... | A01M 1/2077 |
| 2020/0139387 A1* | 5/2020 | Song | ........................ | B05B 12/32 |
| 2025/0001035 A1* | 1/2025 | Turner | .................... | A61L 9/032 |

FOREIGN PATENT DOCUMENTS

| | | | | | |
|---|---|---|---|---|---|
| CN | 106490813 A | * | 3/2017 | ............. | A45D 24/22 |
| CN | 108525083 A | | 9/2018 | | |
| CN | 214807104 U | | 11/2021 | | |
| CN | 113786052 A | * | 12/2021 | ............. | A45D 24/28 |
| CN | 215837552 U | * | 2/2022 | ............. | A45D 24/10 |
| CN | 217366649 U | | 9/2022 | | |
| CN | 115245234 A | * | 10/2022 | ............. | A45D 24/10 |

* cited by examiner

*Primary Examiner* — Darren W Gorman
(74) *Attorney, Agent, or Firm* — George D. Morgan

(57) ABSTRACT

The present utility model provides an essential oil atomization and pumping apparatus, including a control circuit board and a cartridge assembly for essential oil atomization, where the cartridge assembly is electrically connected to the control circuit board, and the cartridge assembly includes a ceramic heating strip for heating an atomized essential oil; the apparatus further includes an air pump assembly for pumping atomized mist from a position of the cartridge assembly to a position of a mist outlet at an outer side, where the air pump assembly includes an air pump unit and an air pump block for delimiting the air pump unit, the air pump unit is interconnected to the cartridge assembly through an air inlet hose, and the cartridge assembly is connected to the mist outlet through a mist outlet hose.

10 Claims, 4 Drawing Sheets

ESSENTIAL OIL ATOMIZATION AND PUMPING APPARATUS

CROSS-REFERENCE TO RELATED APPLICATIONS

The application claims priority to Chinese patent application No. 2024202910890, filed on Feb. 11, 2024, the entire contents of which are incorporated herein by reference.

TECHNICAL FIELD

The present utility model relates to the technical field of atomization and pumping apparatuses, and in particular, to an essential oil atomization and pumping apparatus with an outstanding effect in use.

BACKGROUND

Hairdressing electronic products such as hair straightening combs and hair straighteners are common products used by people in daily life. Generally, a functional feature of the products is to add a sprayer apparatus on the basis of a conventional hairdressing product, to spread a cosmeceutical spray over hair and scalp during hair brushing.

With continuous development and progresses of technologies, existing hairdressing products have been greatly improved and enhanced in aspects of specific functions and structures. Some become easier to hold, and some are upgraded with temperature regulation mechanisms, bringing better user experience. However, there are still some drawbacks. For example, a spray actually mostly relies on atomization by using an atomizer piece, or a spraying effect is improved by using a fan, but the effect is poor, or a specific structural part for atomization has a problem that an effect in use is not good due to relatively poor performance.

For example, in the utility model patent application No. CN202123212048.3 entitled "Spray Hair Straightening Comb", a spray hair straightening comb is specifically disclosed, and includes a shaft and a comb part. The shaft is fixed below the comb part, and the comb part is provided with teeth, where: an upper part of the shaft is provided with a spray opening, an atomizer is disposed in the shaft, and an output end of the atomizer is provided on the spray opening. As the spray opening is provided on the shaft and is kept a specific distance from the teeth, when a spray is spread, the spray does not stick to the teeth, so that a spraying effect is improved.

The foregoing solution in a conventional technology has a problem of a relatively poor spraying effect. To further enhance product performance, a specific aspect of an atomization and spraying structure needs to be improved and enhanced.

SUMMARY

A problem in a conventional technology to be resolved in this application is that:

Although existing hairdressing products have been greatly improved and enhanced in aspects of specific functions and structures, there are still some drawbacks. For example, a spray actually mostly relies on atomization by using an atomizer piece, or a spraying effect is improved by using a fan, but the effect is poor, or a specific structural part for atomization has a problem that an effect in use is not good due to relatively poor performance.

The present utility model resolves the technical problems with the following solutions.

An essential oil atomization and pumping apparatus is provided, and includes a control circuit board and a cartridge assembly for essential oil atomization, where the cartridge assembly is electrically connected to the control circuit board, and the cartridge assembly includes a ceramic heating strip for heating an atomized essential oil.

The apparatus further includes an air pump assembly for pumping atomized mist from a position of the cartridge assembly to a position of a mist outlet at an outer side, where the air pump assembly includes an air pump unit and an air pump block for delimiting the air pump unit, the air pump unit is interconnected to the cartridge assembly through an air inlet hose, and the cartridge assembly is connected to the mist outlet through a mist outlet hose.

The cartridge assembly further includes a cartridge body, a heating strip support that correspondingly fits a shape of the cartridge body, a lower cartridge casing, an oil-absorbent cotton at an inner side of the lower cartridge casing, and a cartridge pin for an electrically conductive connection.

The heating strip support, the oil-absorbent cotton, and the ceramic heating strip are in an inner space surrounded by the cartridge body and the lower cartridge casing that fit into and connected to each other, an oil supply hole corresponding to a position of the ceramic heating strip is provided at an upper part of the heating strip support, and the ceramic heating strip is at an inner side of the oil supply hole.

The apparatus further includes a main body pin disposed on the control circuit board or electrically connected to the control circuit board, where a position of the main body pin corresponds to a position of the cartridge pin.

Preferably, a periphery of the lower cartridge casing is wrapped by a cartridge waterproof gasket, and an outer side of the heating strip support is wrapped by support silica gel.

The apparatus further includes heating strip silica gel for delimiting the ceramic heating strip.

Preferably, the cartridge assembly further includes a cartridge magnet.

A magnet delimiting groove for embedding and accommodating the cartridge magnet is provided at the inner side of the lower cartridge casing. Preferably, the air pump block includes an air pump accommodating groove in the middle and connection pieces at two ends for fixed connections.

The air pump assembly is accommodated in the air pump accommodating groove by snap-fit.

Preferably, a snap fastener or a hook for delimiting the mist outlet hose and/or the air inlet hose is disposed on the air pump block by one-piece molding.

The snap fastener or the hook is at one end of the air pump block or at both ends of the air pump block.

A hose groove for accommodating the hose is formed at an inner side of the snap fastener or the hook.

Preferably, the heating strip support and the lower cartridge casing are movably connected in a detachable manner.

The oil-absorbent cotton is accommodated at the inner side of the lower cartridge casing.

Conductive connection holes at corresponding positions for running through the cartridge pin are provided on the oil-absorbent cotton and the lower cartridge casing.

Preferably, a plurality of snap-fit pieces are disposed by one-piece molding at an outer side of a lower part of the heating strip support.

Snap-fit holes corresponding to the snap-fit pieces are provided on the lower cartridge casing.

Preferably, protruding joints in joint with the air inlet hose and the mist outlet hose are further disposed at the bottom of the lower cartridge casing by one-piece molding.

Both the air inlet hose and the mist outlet hose are provided with elbow connection pieces at one end of the cartridge assembly for connections to the protruding joints.

Preferably, a silica gel groove that corresponds to the heating strip silica gel and that is used to accommodate the heating strip silica gel is provided at an inner side of the heating strip support.

Preferably, an upper part of the heating strip support is protruding upwardly to form an oil supply protruding platform.

A support silica gel hole, corresponding to a position of the oil supply protruding platform, that fits into a shape of the oil supply protruding platform is provided on the support silica gel.

The upper part of the heating strip support is wrapped by the whole support silica gel.

A technical effect achieved in this application by resolving the technical problem is as follows:

Compared with the conventional technology, according to the essential oil atomization and pumping apparatus provided in the present utility model, the control circuit board and the cartridge assembly for essential oil atomization are disposed together, where the cartridge assembly is electrically connected to the control circuit board, and the cartridge assembly includes the ceramic heating strip for heating an atomized essential oil; the apparatus further includes the air pump assembly for pumping atomized mist from a position of the cartridge assembly to a position of a mist outlet at an outer side, where the air pump assembly includes an air pump unit and an air pump block for delimiting the air pump unit, the air pump unit is interconnected to the cartridge assembly through the air inlet hose, and the cartridge assembly is connected to the mist outlet through a mist outlet hose; the cartridge assembly further includes the cartridge body, the heating strip support that correspondingly fits the shape of the cartridge body, the lower cartridge casing, the oil-absorbent cotton at the inner side of the lower cartridge casing, and the cartridge pin for an electrically conductive connection; the heating strip support, the oil-absorbent cotton, and the ceramic heating strip are in the inner space surrounded by the cartridge body and the lower cartridge casing that fit into and connected to each other, the oil supply hole corresponding to the position of the ceramic heating strip is provided at the upper part of the heating strip support, and the ceramic heating strip is at the inner side of the oil supply hole; and the apparatus further includes the main body pin disposed on the control circuit board or electrically connected to the control circuit board, where the position of the main body pin corresponds to the position of the cartridge pin. In actual application, the air pump assembly is used for mist pumping. An application effect is better with higher stability and better user experience.

11: control circuit board; 12: cartridge assembly; 123: heating strip support; 1231: oil supply hole; 1233:

snap-fit piece; 1234: silica gel groove; 124: heating strip silica gel; 125: ceramic heating strip; 126: cartridge pin; 127: cartridge magnet; 128: oil-absorbent cotton; 129: lower cartridge casing; 1292: snap-fit hole; 1293: cartridge waterproof gasket; 1295: magnet delimiting groove; 1297: protruding joint; 13: air pump assembly; 14: mist outlet hose; 141: mist outlet; 15: air inlet hose; 16: air pump block; 161: snap fastener or hook; and 17: elbow connection piece.

DETAILED DESCRIPTION OF THE EMBODIMENTS

To make the purposes, technical solutions, and advantages of the present utility model clearer, the following further describes the present utility model in detail with reference to the accompanying drawings and embodiments. It should be understood that, specific embodiments described herein are merely used to explain the present utility model but not to limit the present utility model.

Figure 1:
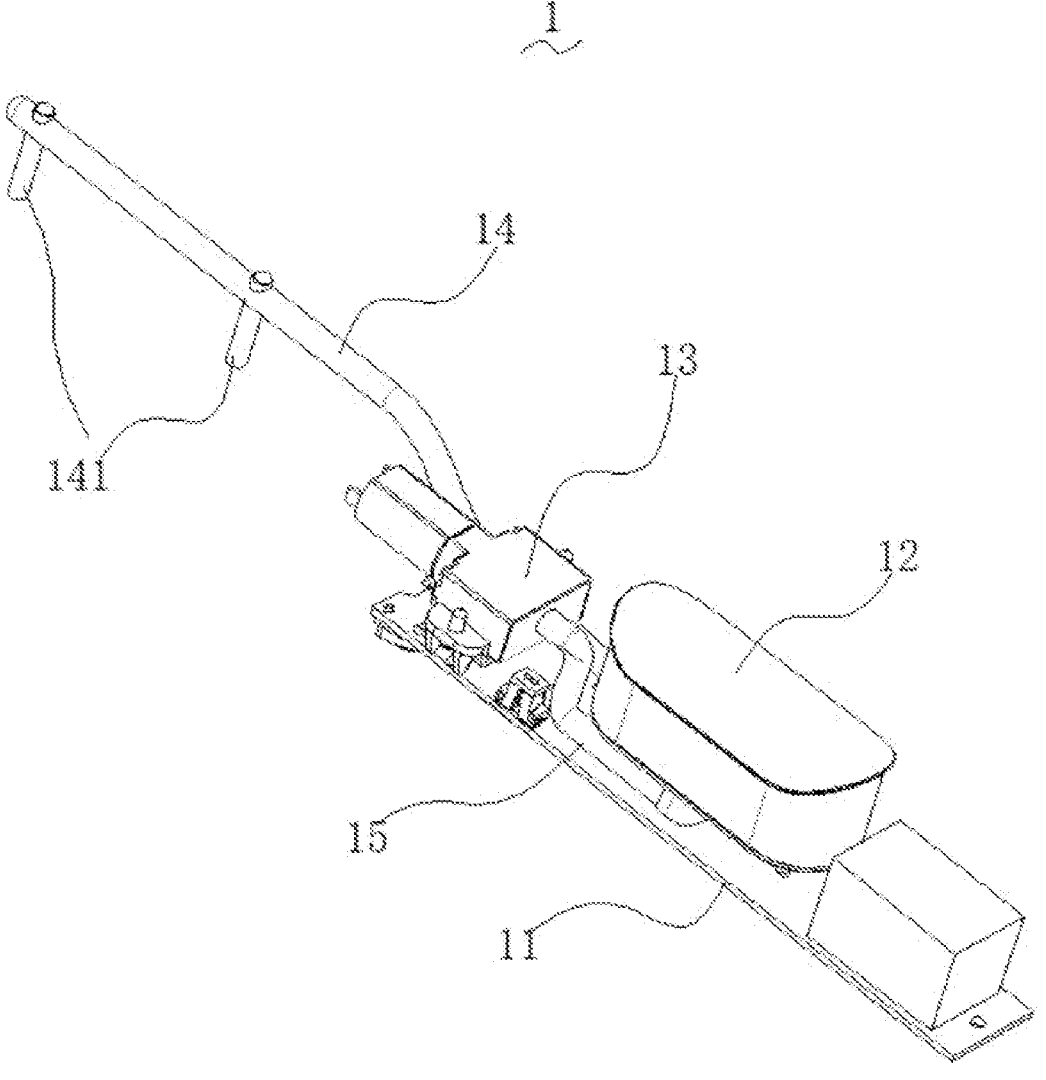
FIG. 1 and FIG. 2 are schematic diagrams of a stereoscopic view of a structure of an essential oil atomization and pumping apparatus according to the present utility model.
Figure 2:
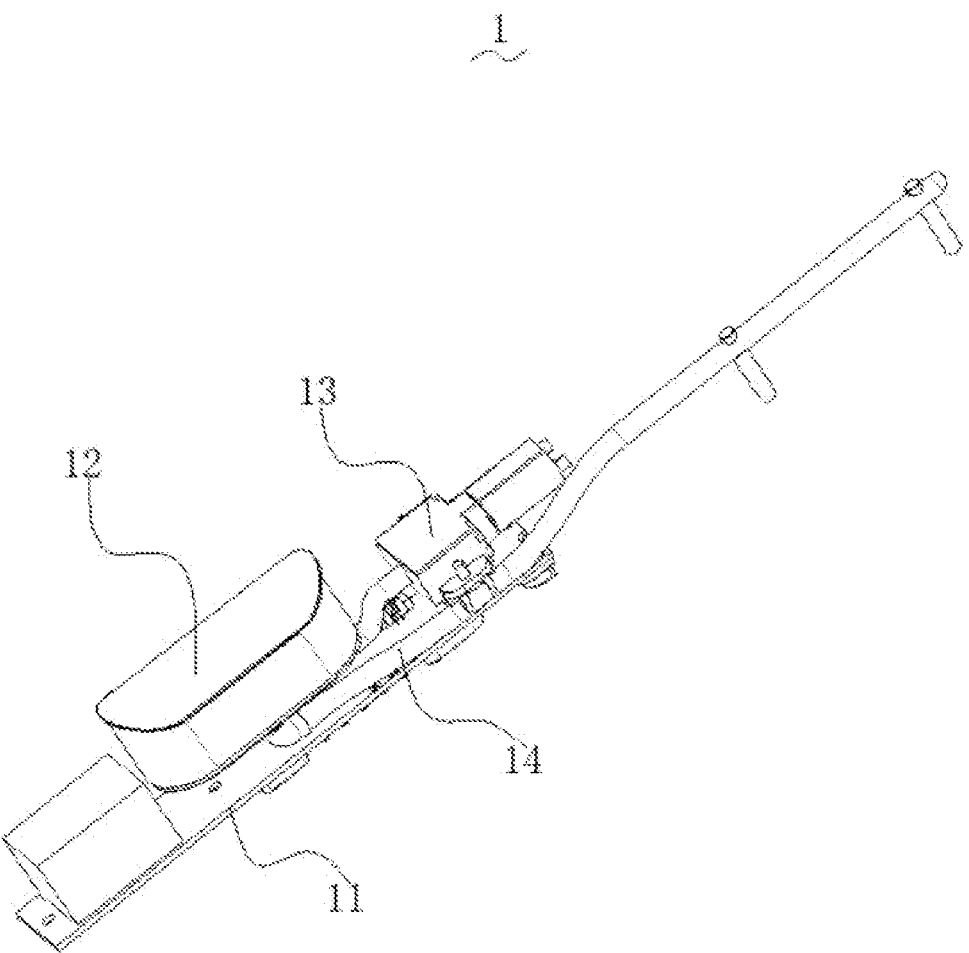
Figure 3:
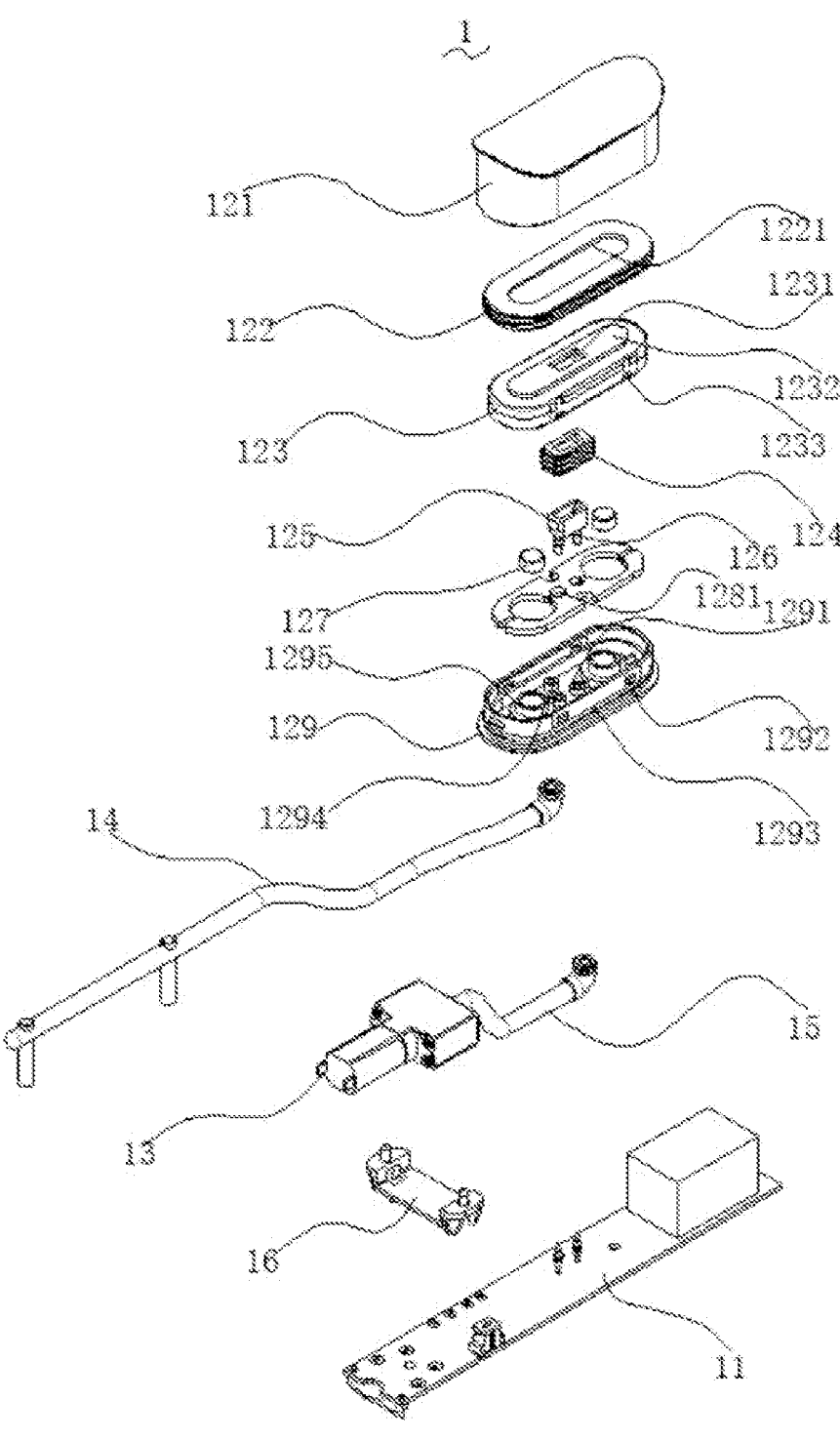
FIG. 3 and FIG. 4 are schematic diagrams of an exploded view of a structure of an essential oil atomization and pumping apparatus according to the present utility model. In the figures.
Figure 4:
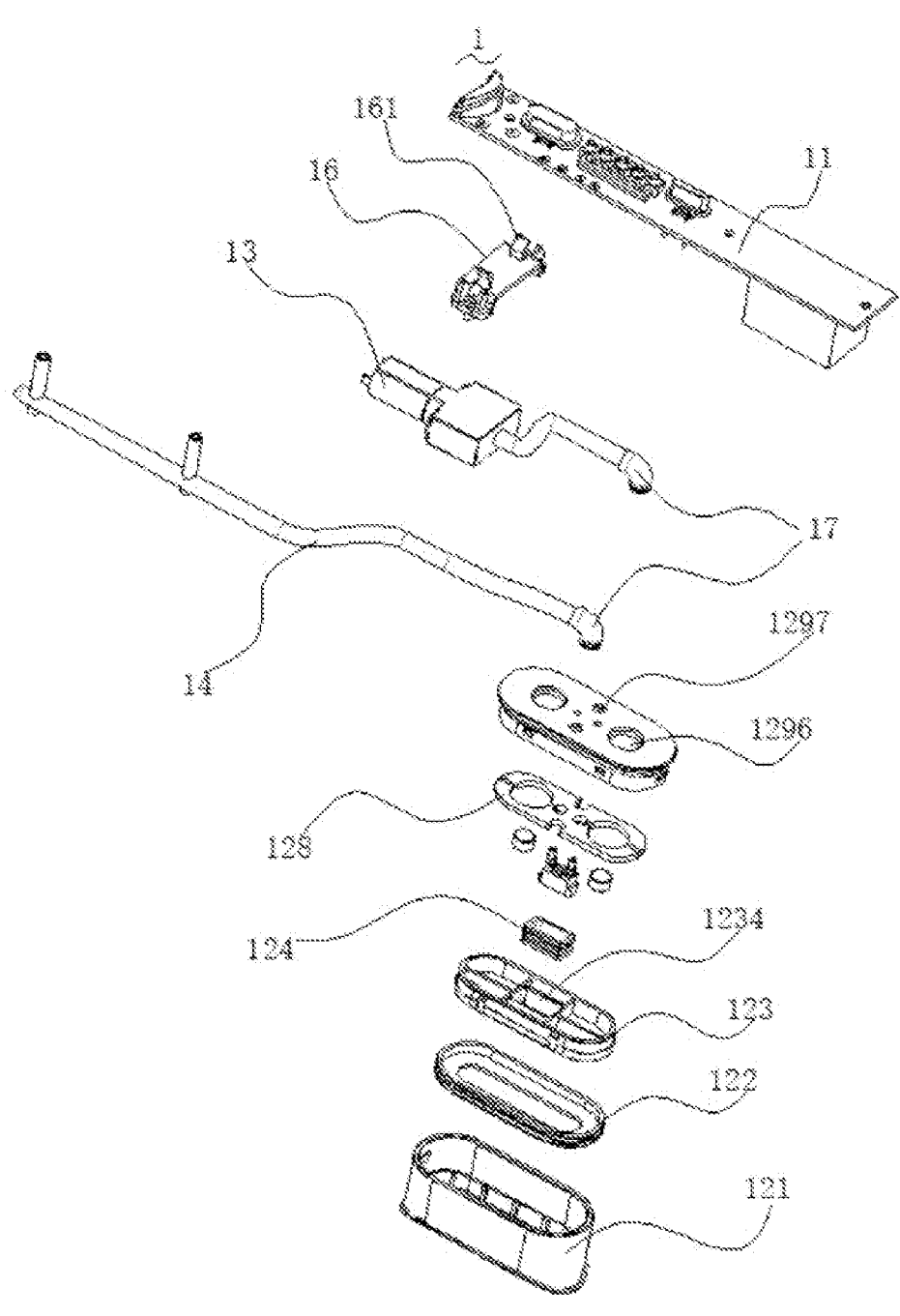

Refer to FIG. 1 to FIG. 4. An essential oil atomization and pumping apparatus 1 provided in the present utility model includes a control circuit board 11 and a cartridge assembly 12 for essential oil atomization, where the cartridge assembly 12 is electrically connected to the control circuit board 11, and the cartridge assembly 12 includes a ceramic heating strip 125 for heating an atomized essential oil. Another functional component similar to the ceramic heating strip 125, for example, a heating sheet, belongs to an equivalent technical solution.

The apparatus further includes an air pump assembly 13 for pumping atomized mist from a position of the cartridge assembly 12 to a position of a mist outlet 141 at an outer side, where the air pump assembly 13 includes an air pump unit and an air pump block 16 for delimiting the air pump unit, the air pump unit is interconnected to the cartridge assembly 12 through an air inlet hose 15, and the cartridge assembly 12 is connected to the mist outlet 141 through a mist outlet hose 14.

The cartridge assembly 12 further includes a cartridge body 121, a heating strip support 123 that correspondingly fits a shape of the cartridge body 121, a lower cartridge casing 129, an oil-absorbent cotton 128 at an inner side of the lower cartridge casing 129, and a cartridge pin 126 for an electrically conductive connection. During actual assembly, the cartridge body 121 directly covers an upper part of the lower cartridge casing 129 to form a sealed inner oil storage space.

The heating strip support 123, the oil-absorbent cotton 128, and the ceramic heating strip 125 are in an inner space surrounded by the cartridge body 121 and the lower cartridge casing 129 that fit into and connected to each other, an oil supply hole 1231 corresponding to a position of the ceramic heating strip 125 is provided at an upper part of the heating strip support 123, and the ceramic heating strip 125 is at an inner side of the oil supply hole 1231.

The apparatus further includes a main body pin disposed on the control circuit board 11 or electrically connected to the control circuit board 11, where a position of the main body pin corresponds to a position of the cartridge pin 126.

In this application, the control circuit board 11 and the cartridge assembly 12 for essential oil atomization are disposed at the same time, where the cartridge assembly 12 is electrically connected to the control circuit board 11, and the cartridge assembly 12 includes the ceramic heating strip 125 for heating an atomized essential oil; the apparatus further includes the air pump assembly 13 for pumping atomized mist from a position of the cartridge assembly 12 to a position of a mist outlet 141 at an outer side, where the air pump assembly 13 includes an air pump unit and an air pump block 16 for delimiting the air pump unit, the air pump unit is interconnected to the cartridge assembly 12 through the air inlet hose 15, and the cartridge assembly 12 is connected to the mist outlet 141 through a mist outlet hose 14; the cartridge assembly 12 further includes the cartridge body 121, the heating strip support 123 that correspondingly fits the shape of the cartridge body 121, the lower cartridge casing 129, the oil-absorbent cotton 128 at the inner side of the lower cartridge casing 129, and the cartridge pin 126 for an electrically conductive connection; the heating strip support 123, the oil-absorbent cotton 128, and the ceramic heating strip 125 are in the inner space surrounded by the cartridge body 121 and the lower cartridge casing 129 that fit into and connected to each other, the oil supply hole 1231 corresponding to the position of the ceramic heating strip 125 is provided at the upper part of the heating strip support 123, and the ceramic heating strip 125 is at the inner side of the oil supply hole 1231; and the apparatus further includes the main body pin disposed on the control circuit board 11 or electrically connected to the control circuit board 11, where the position of the main body pin corresponds to the position of the cartridge pin 126. In actual application, the air pump assembly 13 is used for mist pumping. An application effect is better with higher stability and better user experience.

In some other embodiments, a periphery of the lower cartridge casing 129 is wrapped by a cartridge waterproof gasket 1293, and an outer side of the heating strip support 123 is wrapped by support silica gel 122.

The apparatus further includes heating strip silica gel 124 for delimiting the ceramic heating strip 125.

The cartridge assembly 12 further includes a cartridge magnet 127. There may be one or more cartridge magnets 127, for example, there may be two as shown in the accompanying drawings of this application, and the cartridge magnets are disposed symmetrically.

Magnet delimiting grooves 1295 and 1296 for embedding and accommodating the cartridge magnet 127 are provided at the inner side of the lower cartridge casing 129.

The air pump block 16 includes an air pump accommodating groove in the middle and connection pieces at two ends for fixed connections.

Connection holes are used for screw thread connection and fixation.

The air pump assembly 13 is accommodated in the air pump accommodating groove by snap-fit.

A snap fastener or a hook 161 for delimiting the mist outlet hose 14 and/or the air inlet hose 15 is disposed on the air pump block 16 by one-piece molding.

The snap fastener or the hook 161 is at one end of the air pump block 16 or at both ends of the air pump block 16.

A hose groove for accommodating the hose is formed at an inner side of the snap fastener or the hook 161.

The heating strip support 123 and the lower cartridge casing 129 are movably connected in a detachable manner.

The oil-absorbent cotton 128 is accommodated at the inner side of the lower cartridge casing 129.

Conductive connection holes 1281 and 1291 at corresponding positions for running through the cartridge pin 126 are provided on the oil-absorbent cotton 128 and the lower cartridge casing 129.

A plurality of snap-fit pieces 1233 are disposed by one-piece molding at an outer side of a lower part of the heating strip support 123.

Snap-fit holes 1292 corresponding to the snap-fit pieces 1233 are provided on the lower cartridge casing 129.

Protruding joints 1297 and 1294 in joint with the air inlet hose 15 and the mist outlet hose 14 are further disposed at the bottom of the lower cartridge casing 129 by one-piece molding.

Both the air inlet hose 15 and the mist outlet hose 14 are provided with elbow connection pieces 17 at one end of the cartridge assembly 12 for connections to the protruding joints 1297 and 1294.

A silica gel groove 1234 that corresponds to the heating strip silica gel 124 and that is used to accommodate the heating strip silica gel 124 is provided at an inner side of the heating strip support 123.

An upper part of the heating strip support 123 is protruding upwardly to form an oil supply protruding platform 1232.

A support silica gel hole 1221, corresponding to a position of the oil supply protruding platform 1232, that fits into a shape of the oil supply protruding platform is provided on the support silica gel 122.

The upper part of the heating strip support 123 is wrapped by the whole support silica gel 122.

A technical effect achieved in this application by resolving the technical problem is as follows:

Compared with the conventional technology, according to the essential oil atomization and pumping apparatus 1 provided in the present utility model, the control circuit board 11 and the cartridge assembly 12 for essential oil atomization are disposed together, where the cartridge assembly 12 is electrically connected to the control circuit board 11, and the cartridge assembly 12 includes the ceramic heating strip 125 for heating an atomized essential oil; the apparatus further includes the air pump assembly 13 for pumping atomized mist from a position of the cartridge assembly 12 to a position of a mist outlet 141 at an outer side, where the air pump assembly 13 includes an air pump unit and an air pump block 16 for delimiting the air pump unit, the air pump unit is interconnected to the cartridge assembly 12 through the air inlet hose 15, and the cartridge assembly 12 is connected to the mist outlet 141 through a mist outlet hose 14; the cartridge assembly 12 further includes the cartridge body 121, the heating strip support 123 that correspondingly fits the shape of the cartridge body 121, the lower cartridge casing 129, the oil-absorbent cotton 128 at the inner side of the lower cartridge casing 129, and the cartridge pin 126 for an electrically conductive connection; the heating strip support 123, the oil-absorbent cotton 128, and the ceramic heating strip 125 are in the inner space surrounded by the cartridge body 121 and the lower cartridge casing 129 that fit into and connected to each other, the oil supply hole 1231 corresponding to the position of the ceramic heating strip 125 is provided at the upper part of the heating strip support 123, and the ceramic heating strip 125 is at the inner side of the oil supply hole 1231; and the apparatus further includes the main body pin disposed on the control circuit board 11 or electrically connected to the control circuit board 11, where the position of the main body pin corresponds to the position of the cartridge pin 126. In actual application, the air pump assembly 13 is used for mist pumping. An application effect is better with higher stability and better user experience.

The foregoing implementations of the present utility model do not constitute a limitation on the protection scope of the present utility model. Any modification, equivalent replacement, improvements, etc. made without departing from the spirit and principle of the present utility model shall all fall within the protection scope of the claims of the present utility model.

What is claimed is:

1. An essential oil atomization and pumping apparatus, comprising a control circuit board and a cartridge assembly for essential oil atomization, wherein the cartridge assembly is electrically connected to the control circuit board, and the cartridge assembly comprises a ceramic heating strip for heating an atomized essential oil, wherein the apparatus further comprises an air pump assembly for pumping atomized mist from a position of the cartridge assembly to a position of a mist outlet at an outer side, wherein the air pump assembly comprises an air pump unit and an air pump block for delimiting the air pump unit, the air pump unit is interconnected to the cartridge assembly through an air inlet hose, and the cartridge assembly is connected to the mist outlet through a mist outlet hose;

the cartridge assembly further comprises a cartridge body, a heating strip support that correspondingly fits a shape of the cartridge body, a lower cartridge casing, an oil-absorbent cotton at an inner side of the lower cartridge casing, and a cartridge pin for an electrically conductive connection;

the heating strip support, the oil-absorbent cotton, and the ceramic heating strip are in an inner space surrounded by the cartridge body and the lower cartridge casing that fit into and connect to each other, an oil supply hole corresponding to a position of the ceramic heating strip is provided at an upper part of the heating strip support, and the ceramic heating strip is at an inner side of the oil supply hole; and the apparatus further comprises a main body pin disposed on the control circuit board or electrically connected to the control circuit board, wherein a position of the main body pin corresponds to a position of the cartridge pin.

2. The essential oil atomization and pumping apparatus according to claim 1, wherein a periphery of the lower cartridge casing is wrapped by a cartridge waterproof gasket, and an outer side of the heating strip support is wrapped by support silica gel; and the apparatus further comprises heating strip silica gel for delimiting the ceramic heating strip.

3. The essential oil atomization and pumping apparatus according to claim 1, wherein the cartridge assembly further comprises a cartridge magnet; and a magnet delimiting groove for embedding and accommodating the cartridge magnet is provided at the inner side of the lower cartridge casing.

4. The essential oil atomization and pumping apparatus according to claim 1, wherein the air pump block comprises an air pump accommodating groove in the middle and connection pieces at two ends for fixed connections; and the air pump assembly is accommodated in the air pump accommodating groove by snap-fit.

5. The essential oil atomization and pumping apparatus according to claim 4, wherein a snap fastener or a hook for delimiting the mist outlet hose and/or the air inlet hose is disposed on the air pump block by one-piece molding;

the snap fastener or the hook is at one end of the air pump block or at both ends of the air pump block; and a hose groove for accommodating the hose is formed at an inner side of the snap fastener or the hook.

6. The essential oil atomization and pumping apparatus according to claim 1, wherein the heating strip support and the lower cartridge casing are movably connected in a detachable manner;

the oil-absorbent cotton is accommodated at the inner side of the lower cartridge casing; and conductive connection holes at corresponding positions for running through the cartridge pin are provided on the oil-absorbent cotton and the lower cartridge casing.

7. The essential oil atomization and pumping apparatus according to claim 6, wherein a plurality of snap-fit pieces are disposed by one-piece molding at an outer side of a lower part of the heating strip support; and snap-fit holes corresponding to the snap-fit pieces are provided on the lower cartridge casing.

8. The essential oil atomization and pumping apparatus according to claim 1, wherein protruding joints in joint with the air inlet hose and the mist outlet hose are further disposed at the bottom of the lower cartridge casing by one-piece molding; and both the air inlet hose and the mist outlet hose are provided with elbow connection pieces at one end of the cartridge assembly for connections to the protruding joints.

9. The essential oil atomization and pumping apparatus according to claim 2, wherein a silica gel groove that corresponds to the heating strip silica gel and that is used to accommodate the heating strip silica gel is provided at an inner side of the heating strip support.

10. The essential oil atomization and pumping apparatus according to claim 2, wherein an upper part of the heating strip support is protruding upwardly to form an oil supply protruding platform;

a support silica gel hole, corresponding to a position of the oil supply protruding platform, that fits into a shape of the oil supply protruding platform is provided on the support silica gel; and the upper part of the heating strip support is wrapped by the whole support silica gel.

* * * * *